United States Patent [19]

Mynderse et al.

[11] Patent Number: 4,612,330

[45] Date of Patent: Sep. 16, 1986

[54] ANTIINFLAMMATORY METHOD

[75] Inventors: Jon S. Mynderse; Rosanne Bonjouklian, both of Indianapolis, Ind.

[73] Assignee: Eli Lilly and Company, Indianapolis, Ind.

[21] Appl. No.: 697,997

[22] Filed: Feb. 4, 1985

[51] Int. Cl.[4] .............................................. A61K 31/19
[52] U.S. Cl. .................................................... 514/557
[58] Field of Search ......................................... 514/557

[56] References Cited

PUBLICATIONS

Patrick T. K. Yu, Undergraduate Symposium of the 183rd American Chemical Society Meeting, Las Vegas, Nevada, Mar. 28–Apr. 2, 1982 (Abstract CHED 32).
Derwent 84-109140/18, Abstracting EPO 106,576.
Kikuchi et al., *Tetrahedron Letters*, 23 (49), 5171 (1982).

*Primary Examiner*—Stanley J. Friedman
*Attorney, Agent, or Firm*—Robert A. Conrad

[57] ABSTRACT

This invention provides a method of treating inflammation and arthritis employing certain prostanoic acid derivatives. Pharmaceutical formulations employing these derivatives are also provided.

3 Claims, No Drawings

ANTIINFLAMMATORY METHOD

BACKGROUND OF THE INVENTION

During the past 20 years, a variety of prostaglandin derivatives have been synthesized and isolated from natural sources. The compounds are generally quite potent and possess a variety of pharmacological properties. See Nelson, et al., *Chemical and Engineering News,* 30 (Aug. 16, 1982). See also "Practical Applications of Prostaglandins", (S. M. M. Karim, Ed.), University Park Press, Baltimore, 1979. Many prostaglandins which either have interesting biological properties or are intermediates to other prostaglandins have been isolated from marine animals such as coral. See W. P. Schneider in "Prostaglandins: Chemical and Biochemical Aspects", p. 4, University Park Press, Baltimore, 1976; Nelson, et al., supra, at page 32; H. Kikuchi, et al., *Tetrahedron Letters,* 23 (49), 5171 (1982). Since small changes in chemical structure have been shown to produce large differences in biological potency and utility, new derivatives of prostaglandins hold the promise that useful drugs may be found.

SUMMARY OF THE INVENTION

This invention provides a method of treating inflammation and arthritis in mammals which comprises administering to said mammal an effective amount of Punaglandin-1 (PG-1) or Punaglandin-2 (PG-2).

This invention also provides pharmaceutical formulations comprising PG-1 or PG-2 in combination with a suitable pharmaceutical carrier, diluent, or excipient therefor. The formulations provided by this invention are particularly useful in treating inflammation and arthritis in mammals.

DETAILED DESCRIPTION

Punaglandin-1 and -2 are prostanoic acid derivatives isolated from the coral *Telesto riisei*. They are the first known naturally occurring halogenated prostanoids and were reported by Patrick T. K. Yu et al. at an undergraduate symposium of the 183rd American Chemical Society National Meeting in Las Vegas, Nev. in the Spring of 1982 (see Abstract CHED32). Punaglandin-1 was identified as 5,6,7-tris(acetyloxy)-7-(4-chloro-2-hydroxy-2-[2(Z),5(Z)-octadienyl]-5-oxo-3-cyclopenten-1-yl)heptanoic acid, methyl ester, while Punaglandin-2 was determined to be 5,6,7-tris(acetyloxy)-7-(4-chloro-2-hydroxy-2-[2-(Z)-octenyl]-5-oxo-3-cyclopenten-1-yl)heptanoic acid, methyl ester. No utility for these two compounds was disclosed at the ACS meeting nor has any other description of these compounds appeared in the literature.

Punaglandin-1 was isolated according to the following procedure.

Freeze-dried *Telesto riisei* (360 g) was extracted with hexane in a Soxhlet apparatus. The residue (5.7 g) was partitioned between hexane and 8:2 (v/v) methanol/water. The product obtained from evaporating the aqueous methanol layer (2.4 g) was chromatographed over silica gel eluting with 6:4 (v/v) hexane/ethyl acetate. The appropriate fraction, having a $\lambda_{max}$ of 228 nm ($\epsilon$ 7,900, methanol) was collected and evaporated to dryness. The product was purified by reversed phase $C_{18}$ HPLC, eluting with 8:2 (v/v) methanol/water. Evaporation of the appropriate fraction provided 600 mg of punaglandin-1 as a colorless oil. The material had the following physical characteristics:

Composition: $C_{27}H_{37}ClO_{10}$ (m wt 556.5).
Rotation: $[\alpha]_D = +10.6°$ (c=2.4, MeOH).
UV max (MeOH): 228 nm ($\epsilon$ 7,900).
IR max ($CHCl_3$): 3500, 3430, 2930, 2860, 1740, 1610, 1375, 1235, 1025 $cm^{-1}$.

$^1H$ NMR ($CDCl_3$, 500 MHz): $\delta$ 7.26 (1H, H-11, s); 5.61 (1H, H-6, dd, J=5, 5 Hz); 5.61 (1H, H-15, dtt, J=10.8, 7, 1 Hz); 5.41 (1H, H-18, dtt, J=10.6, 7, 1 Hz); 5.34 (1H, H-7, dd, J=5, 5 Hz); 5.30 (1H, H-14, dddt, J=10.8, 7.0, 8.1, 1 Hz); 5.24 (1H, H-17, dtt, J=10.6, 7, 1 Hz); 5.18 (1H, H-5, ddd, J=5, 5, 7.5 Hz); 3.65 (3H, OMe, s); 2.77 (2H, H-16, dddd, J=7, 7, 1, 1Hz); 2.75 (1H, H-8, d, J=5 Hz); 2.53 (1H, H-13a, dd, J=7.0, 14.7 Hz); 2.45 (1H, H-13b, dd, J=8.1, 14.7 Hz); 2.34 (1H, H-2a, dt, J=15.5, 7 Hz); 2.29 (1H, H-2b, dt, J=15.5, 7 Hz); 2.11 (3H, OAc, s); 2.08 (3H, OAc, s); 2.05 (2H, ddq, J=7, 1, 7 Hz); 2.00 (3H, OAc, s); 1.52–1.72 (4H, H-3 & H-4, br m); 1.00 (3H, H-20, t, J=7.5 Hz).

Punaglandin-1

$^{13}C$ NMR ($CDCl_3$, 125 MHz): $\delta$ 196 (s), 173.8 (s), 171.3 (s), 170.5 (s), 170.4 (s), 158.1 (d), 136.1 (s), 134.6 (d), 132.9 (d), 126.0 (d), 121.5 (d), 77.2 (s), 72.9 (d), 71.6 (d), 70.0 (d), 53.4 (d), 51.8 (q), 39.4 (t), 33.5 (t), 30.1 (t), 25.8 (t), 21.1 (q), 21.0 (q), 20.9 (q), 20.7 (t), 20.2 (t), 14.3 (q).

Punaglandin-2 was isolated in the same manner. On reverse phase $C_{18}$ HPLC (methanol/water, 3:1), PG-2 elutes after PG-1. The yields of the two compounds are generally in a ratio of 3:1 PG-1:PG-2. Punaglandin-2 was isolated as a colorless oil having the following characteristics:

Composition: $C_{27}H_{39}ClO_{10}$ (m wt 558.5).
Rotation: $[\alpha]_D = +8.8°$ (c=1.9, MeOH).
UV max (MeOH): 227 nm ($\epsilon$ 7,500).
IR max ($CH_2Cl_2$): 3420 (broad), 2920, 1730 (broad), 1375, 1230, 1045 $cm^{-1}$.

$^1H$ NMR ($CDCl_3$, 500 MHz): $\delta$ 7.26 (1H, H-11, s); 5.63 (1H, H-15, ddt, J=10.9, 7, 1 Hz); 5.61 (1H, H-6, dd, J=5, 5 Hz); 5.31 (1H, H-7, dd, J=5, 5 Hz); 5.25 (1H, H-14, ddd, J=10.9, 7.9, 7.3 Hz); 5.18 (1H, H-5, ddd, J=5, 5, 7.5 Hz); 3.65 (3H, $OCH_3$, s); 3.48 (1H, OH, s exchangeable)); 2.74 (1H, H-8, d, J=5 Hz); 2.48 (1H, H-13a, dd, J=14.4, 7.3 Hz); 2.40 (1H, H-13b, dd, J=14.4, 7.9 Hz); 2.33 (1H, H-2a, dt, J=15.5, 7 Hz); 2.27 (1H, H-2b, dt, J=15.5, 7 Hz); 2.09 (3H, OAc, s); 2.06 (3H, OAc, s); 2.06 (3H, OAc, s); 1.98 (3H, OAc, s); 1.95 (2H, H-16, dt, J=7, 7 Hz); 1.52–1.72 (4H, H-3 & H-4, br m); 1.26 (6H, H-17, 18, 19, m); 0.85 (3H, H-20, t, J=6.7 Hz).

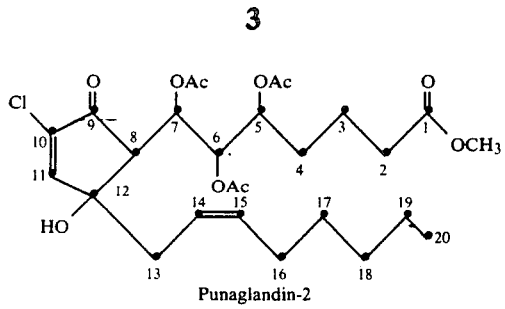

Punaglandin-2

$^{13}$C NMR (CDCl$_3$, 125 MHz): δ196.0 (s), 173.8 (s), 171.9 (s), 170.6 (s), 170.4 (s), 158.2 (d), 136.8 (s), 136.0 (d), 121.1 (d), 77.2 (s), 72.9 (d), 71.7 (d), 70.0 (d), 53.5 (d), 51.9 (q), 39.5 (t), 33.5 (t), 31.7 (t), 30.2 (t), 29.3 (t), 27.6 (t), 22.7 (t), 21.1 (q), 21.0 (q), 20.9 (q), 20.2 (t), 14.2 (q).

It has now been discovered that Punaglandin-1 and -2 are useful in the treatment of inflammation and arthritis in mammals. The anti-inflammatory activity of PG-1 and PG-2 has been demonstrated in the carrageenin-induced edema test method described by C. A. Winter, Proc. Soc. Exp. Biol. Med., 111, 544 (1962). In this method, inflammation is induced by injecting carrageenin into one of the hind paws of rats. Test compounds were administered prior to the carrageenin injection to determine the percent inhibition of the subsequent inflammation, in comparison with the animals' contralateral (control) paws. Punaglandin-1 inhibited paw swelling 79.6% and 62.1% when dosed at 50 mg/kg by the intraperitoneal and subcutaneous routes, respectively.

Developing adjuvant-induced arthritis test in rats

The compounds were also tested for their ability to alter hind paw swelling and bone damage resulting from adjuvant-induced arthritis in rats. In order to quantitate the inhibition of hind paw swelling resulting from adjuvant-induced arthritis, two phases of inflammation have been defined: (1) the primary and secondary *injected* hind paw, and (2) the secondary *uninjected* hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Adjuvant arthritis was induced in male Lewis-Wistar rats (200-210 grams) by a single subplantar injection into the right hind paw of 0.1 ml of a 0.5% suspension of heat-killed, lyophilized *Mycobacterium tuberculosis* (Calbiochem-Perrigen-C) in mineral oil (a modification of a method reported by Winter et al., Arth. Rheum., 9, 394-397 (1966)). One group of 10 rats ("TB control") received only this treatment. Another group of 5 rats received no treatment (normal control). Each compound to be tested was suspended in carboxy-methylcellulose (1%) and administered i.p. to rats (group of 5) in daily doses of 10 mg/kg beginning on day one and continuing through the 28th day after the adjuvant injection (29 doses). Paw volumes were measured by mercury displacement using a Statham pressure transducer and digital voltmeter. Volumes of both the injected and the uninjected hind paws were measured on days 16, 18, 21, 23, 25, 28, and 30. X-ray photos were taken on day 30, after the animals were sacrificed. The paw volume measurements on the uninjected paw beginning with day 16 through day 30 were computer plotted for the TB controls, the normal controls, and the drug-treated animals, and the areas under the curves [(TB controls minus normal controls) and (treated animals minus normal controls)] were determined. The results are summarized in Table I.

TABLE I

| Inhibition of Uninjected Paw Volume Inflammation Days 16 through 30 | | |
|---|---|---|
| Compound | Dose mg./kg. I.P. × 29 | % Inhibition* |
| PG-1 | 10 | 56.7 |

*% inhibition is the difference of the areas under the curves (AUC) of the mean uninjected paw volumes plotted for days 16, 18, 21, 23, 25, 28 and 30 according to the following formula:

$$\% \text{ inhibition} = \left[1 - \frac{\text{(Drug treated AUC)} - \text{(normal control AUC)}}{\text{(TB control AUC)} - \text{(normal control AUC)}}\right] \times 100$$

Gross observation of X-ray photos taken of uninjected paws showed considerable inhibition of bone damage in the treated animals as compared to the TB control group. A substantial inhibition of bond damage was also seen in a comparison of the injected paws. The inhibition of bond damage is a demonstration of anti-arthritic activity.

The compounds employed in the method of this invention may be administered by various routes including the oral, rectal, transdermal, subcutaneous, intravenous, intramuscular, or intranasal routes. The compounds are usually employed in the form of pharmaceutical compositions. Such compositions are prepared in a manner well known in the pharmaceutical art and comprise an effective amount of PG-1 or PG-2. Accordingly, the invention includes a pharmaceutical composition comprising as active ingredient Punaglandin-1 or Punaglandin-2 associated with a pharmaceutically acceptable excipient, diluent, or carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions usually contain as active ingredient from about 1% to about 95% by weight of PG-1 or PG-2 and are preferably formulated in a unit dosage form, each dosage containing from about 0.5 to about 500 mg, more usually about 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 30 mg/kg of body weight. In the treatment of adult humans, a range of from about 0.020 to about 5 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following examples are illustrative of the claimed compositions.

EXAMPLE 1

Hard gelatin capsules are prepared using the following ingredients:

|  | Quantity (mg/capsule) |
| --- | --- |
| Punaglandin-1 | 250 |
| Starch dried | 200 |
| Magnesium stearate | 10 |

The above ingredients are mixed and filled into hard gelatin capsules in 460 mg quantities.

EXAMPLE 2

A tablet formula is prepared using the ingredients below:

|  | Quantity (mg/tablet) |
| --- | --- |
| Punaglandin-2 | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

An aerosol solution is prepared containing the following components:

|  | Weight % |
| --- | --- |
| Punaglandin-1 | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 4

Tablets each containing 60 mg of active ingredient are made up as follows:

| Punaglandin-2 | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 5

Capsules each containing 80 mg of medicament are made as follows:

| Punaglandin-2 | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories each containing 225 mg of active ingredient are made as follows:

| Punaglandin-1 | 225 mg |
| --- | --- |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 50 mg of medicament per 5 ml dose are made as follows:

| Punaglandin-1 | 50 mg |
| --- | --- |
| Sodium carboxymethyl cellulose | 50 mg |
| Syrup | 1.25 ml |
| Benzoic acid solution | 0.10 ml |

| | |
|---|---|
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

We claim:

1. A method of treating inflammation and arthritis in mammals which comprises administering to said mammal an effective amount of Punaglandin-1 or Punaglandin-2.

2. The method according to claim 1 employing Punaglandin-1.

3. The method according to claim 1 employing Punaglandin-2.

* * * * *